(12) United States Patent
Candiani et al.

(10) Patent No.: US 6,211,192 B1
(45) Date of Patent: Apr. 3, 2001

(54) ALKYNYL-SUBSTITUTED CAMPTOTHECINS AND PROCESS FOR THEIR PREPARATION

(75) Inventors: Ilaria Candiani, Busto Arsizio; Angelo Bedeschi, Milan; Giuseppina Visentin, Rho; Maria Chiara Fagnola, Piacenza; Laura Capolongo, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/355,952
(22) PCT Filed: Feb. 4, 1998
(86) PCT No.: PCT/EP98/00649
  § 371 Date: Aug. 12, 1999
  § 102(e) Date: Aug. 12, 1999
(87) PCT Pub. No.: WO98/35969
  PCT Pub. Date: Aug. 20, 1998

(30) Foreign Application Priority Data

Feb. 12, 1997 (GB) .................................................. 9702807

(51) Int. Cl.[7] .................. A61K 31/4745; C07D 491/22; A61P 35/00
(52) U.S. Cl. .............................. 514/283; 514/63; 546/14; 546/48
(58) Field of Search ........................ 514/63, 283; 546/14, 546/48

(56) References Cited

U.S. PATENT DOCUMENTS

| 5,602,141 | 2/1997 | Bedeschi et al. . |
| 5,614,628 | 3/1997 | Cabri et al. . |
| 5,801,167 | 9/1998 | Bedeschi et al. . |
| 5,840,899 | 11/1998 | Bedeschi et al. . |
| 5,856,333 | 1/1999 | Cabri et al. . |
| 5,916,897 | 6/1999 | Cabri et al. . |

FOREIGN PATENT DOCUMENTS

93/08189 * 4/1993 (WO) .

* cited by examiner

*Primary Examiner*—Evelyn Mei Huang
(74) *Attorney, Agent, or Firm*—Oblon, Spivak, McClelland, Maier & Neustadt, P.C.

(57) ABSTRACT

The present invention relates to alkynyl-substituted camptothecins of formula (I) wherein X, $R_1$, $R_2$ are as defined herein, and the pharmaceutically salts thereof. These compounds are useful in therapy as antitumor agents.

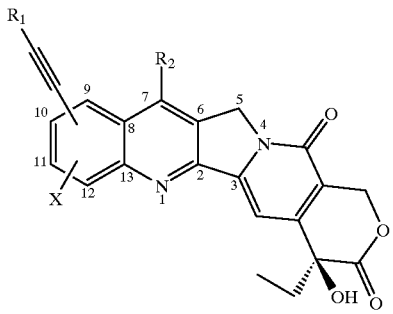

(I)

9 Claims, No Drawings

ALKYNYL-SUBSTITUTED CAMPTOTHECINS AND PROCESS FOR THEIR PREPARATION

This application is the national phase of PCT/EP98/00649 filed Feb. 4, 1998.

The present invention relates to new substituted camptothecin derivatives possessing antitumor activity, to process for their preparation, and to pharmaceutic compositions containing them.

Camptothecin and some of its analogs display potent antitumor activity by the inhibition of Topoisomerase I, that is an enzyme involved in some important cellular functions and cellular growth (see, for instance, Wani et al., J. Med. Chem. 1987, 30, 1774; Hsiang et al., Cancer Res. 1989, 49, 4385; Cancer Res. 1989, 49, 1465). Anticancer activity of Camptothecin both in vitro and in vivo is significantly greater for the lactone versus the carboxylate form (as disclosed, for instance, by W. J. Slichenmyer et al., in "The Current Status of Camptothecin Analogues as Antitumor Agents", J. Natl. Cancer Inst. 1993, 85, 271–291, and references therein), since a closed α-hydroxy lactone ring is an important structural requirement for both passive diffusion of drug into cancer cells, as well as for successful drug interaction with the pharmacological target.

It has recently been pointed out that, in the presence of biologically relevant levels of human albumin, the biologically active form of camptothecin has a very short half-life (about 12 min.), and 2 hours after drug addition to human plasma, a percentage greater than 99% of the drug has converted to camptothecin carboxylate, the biologically inactive and potentially toxic form of the drug (see Burke, G. T.; Mi, Z. "The Structural Basis of Camptothecin Interactions with Human Serum Albumin: Impact on Drug Stability", J. Med. Chem. 1994, 37, 40–46). The same authors disclose also the importance of the substitution in 9 and 7 positions on the camptothecin nucleus in order to improve drug stability in the presence of albumin.

There is therefore a need to find new camptothecin derivatives that have high intrinsic potency, and may gain, at the same time, stability in the presence of serum albumin.

Accordingly, the present invention relates to alkynyl-substituted camptothecins of formula (I)

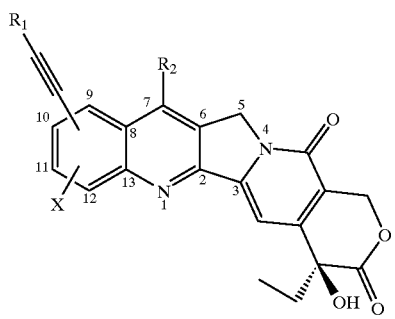

(I)

wherein:
$R_1$ is selected from:
hydrogen;
an optionally substituted $C_1$–$C_6$ alkyl;
$C_3$–$C_7$ cycloalkyl;
$C_3$–$C7$ cycloalkyl $C_1$–$C_6$ alkyl;
phenyl C1–C6 alkyl;
an optionally substituted phenyl;
an optionally substitued naphthyl;
—R, —$NR_3R_4$, wherein $R_x$ is $C_1$–$C_4$ alkylene, $R_3$ and $R_4$ are, each independently, hydrogen, $C_1$–$C_6$ alkyl, phenyl, or benzyl;
—$(R_y)_m$—$COOR_5$, wherein m is zero or 1, $R_y$ is $C_1$–$C_4$ alkylene, $R_5$ is hydrogen, $C_1$–$C_6$ alkyl, $C_3$–$C_7$ cycloalkyl, or phenyl $C_1$–C6 alkyl;
—$(R_z)_n$—$COR_6$, wherein n is zero or 1, $R_z$ is $C_1$–$C_4$ alkylene, $R_6$ is $C_1$–$C_6$ alkyl, $C_3$–$C_7$ cycloalkyl, phenyl $C_1$–$C_6$ alkyl, an optionally substituted phenyl, or —$NR_7R_8$, wherein $R_7$ and $R_8$ are, each independently, hydrogen or $C_1$–$C_6$ alkyl; and
—$SiR_9R_{10}R_{11}$, wherein $R_9$, $R_{10}$ and $R_{11}$ are, each independently, $C_1$–$C_4$ alkyl;
$R_2$ is selected from:
hydrogen; $C_1$–$C_6$ alkyl; $C_3$–$C_7$ cycloalkyl; and phenyl $C_1$–$C_6$ alkyl;
X is selected from:
hydrogen; $C_1$–$C_6$ alkyl; $C_3$–$C_7$ cycloalkyl; $C_1$–$C_6$ alkoxy; $C_3$–$C_7$ cycloalkoxy; $C_1$–$C_6$ alkanoyloxy; benzoyloxy; amino; hydroxy; nitro; chlorine; and a methylene- or ethylene-dioxy group linked to positions 10 and 11 of the molecule; and the pharmaceutically acceptable salts thereof.

In the formulae of the present specification, a dotted line ◄ indicates a substituent below the plane of the ring, while a wedged line ···ıɪɪɪ indicates a substituent above the plane of the ring.

Pharmaceutically acceptable salts according to the present invention are the salts with pharmaceutically acceptable acids, both inorganic acids such as, e.g. hydrochloric, sulfuric, phosphoric, diphosphoric, hydrobromic or nitric acid, and organic acids such as, e.g., citric, fumaric, maleic, malic, ascorbic, succinic, tartaric, benzoic, acetic, trifluoroacetic, methanesulfonic, ethanesulfonic, benzenesulfonic, or p-toluensulfonic acid.

Pharmaceutically acceptable salts of the compounds of formula (I) containing an acid group, i.e. carboxy, with pharmaceutically acceptable bases are also included in the scope of the present invention. Pharmaceutically acceptable bases may be both inorganic bases such as, for instance, alkali metal, e.g. sodium or potassium, or alkaline earth metal, e.g. calcium or magnesium, hydroxides, and organic bases such as, for instance, alkyl amines, e.g. methylamine or triethylamine, aralkylamines, e.g. benzylamine, dibenzylamine, α- or β-phenyl-ethylamine, or heterocyclic amines such as, e.g., piperidine, 1-methyl-piperidine, piperazine or morpholine.

An optionally substituted phenyl may be represented by a group

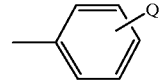

wherein Q, linked to ortho, meta or para position of the phenyl ring, represents hydrogen, $C_1$–$C_6$ alkyl, $C_1$–$C_6$ alkoxy, $C_1$–$C_6$ alkanoyloxy, nitro, amino, mono- or di-alkylamino with from 1 to 6 carbon atoms in the alkyl moiety, tolylsulfonylamino or chlorine, or Q represents a 5 or 6 membered aromatic heterocycle with one or two heteroatoms selected among nitrogen, oxygen or sulphur, optionally mono- or di-substituted by $C_1$–$C_6$ alkyl groups. Examples of the said heterocycles are, for instance, pyrrole, imidazole, pyrazole, isothiazole, isoxazole, furan, thiophene, pyridine, pyrazine, pyrimidine and the like.

Preferably, Q is hydrogen, $C_1$–$C_4$ alkyl, $C_1$–$C_4$ alkoxy, amino, tolylsulfonylamino, chlorine, or Q represents an optionally substituted pyrrole. Particularly preferred values of Q are hydrogen, methoxy, amino, tosylamino, 2,5-dimethylpyrrol-1-yl and chlorine.

An optionally substituted naphthyl is a naphth-1-yl or naphth-2-yl group optionally substituted by $C_1$–$C_6$ alkyl or alkoxy groups.

In the present specification, the hydrocarbon chain of the alkyl, alkylene, alkoxy, and alkanoyloxy groups may be a straight or branched chain. Preferably, $C_1$–$C_6$ alkyl is $C_1$–$C_4$ alkyl, e.g. methyl, ethyl, n-propyl, i-propyl, n-butyl, i-butyl, sec-butyl or t-butyl. More preferably, $C_1$–$C_4$ alkyl is methyl, ethyl or propyl. The $C_1$–$C_6$ alkyl may be substituted, e.g., by hydroxy, alkoxy, phenoxy, thioalkyl, amino, or alkylamino groups. Preferably, $C_3$–$C_7$ cycloalkyl is $C_4$–$C_6$ cycloalkyl, e.g. cyclobutyl, cyclopentyl or cyclohexyl. Preferably, $C_3$–$C_7$ cycloalkyl $C_1$–$C_6$ alkyl is cyclopentylmethyl, cyclohexylmethyl, 2-cyclopentylethyl, 2-cyclohexylethyl, 3-cyclopentylpropyl or 3-cyclohexylpropyl. Preferably, $C_1$–$C_4$ alkylene is, e.g., methylene, ethylene, n-propylene, 1-methyl-ethylene, n-butylene, 1,1-dimethyl-ethylene, 1,2-dimethyl-ethylene, or 1-methyl-propylene. Preferably, $C_1$–$C_6$ alkoxy is $C_1$–$C_4$ alkoxy, e.g. methoxy, ethoxy or propoxy. Preferably, $C_1$–$C_6$ alkanoyloxy is $C_1$–$C_4$ alkanoyloxy, e.g. methanoyloxy, ethanoyloxy or propanoyloxy. A preferred class of compounds according to this invention is represented by compounds of the above formula (I) wherein;

$R_1$ is selected from:
hydrogen; $C_1$–$C_4$ alkyl; phenyl $C_1$–$C_6$ alkyl; phenyl; —$R_x$—$NR_3R_4$, wherein $R_x$ is a $C_1$–$C_4$ alkylene, $R_3$ and $R_4$ are, each independently, $C_1$–$C_4$ alkyl; —$(R_y)_m$—$COOR_5$, wherein m is zero or 1, $R_y$, is a $C_1$–$C_4$ alkylene, $R_5$ is hydrogen or $C_1$–$C_4$ alkyl; and —$(R_z)_n$—$COR_6$, wherein n is zero or 1, $R_z$ is a $C_1$–$C_4$ alkylene, $R_6$ is $C_1$–$C_6$ alkyl, phenyl, or —$NR_7R_8$, wherein $R_7$ and $R_8$ are hydrogen; and —$SiR_9R_{10}R_{11}$, wherein $R_9$, $R_{10}$ and $R_{11}$ are methyl or ethyl;

$R_2$ is hydrogen or $C_1$–$C_4$ alkyl;

X is selected from:
hydrogen; amino; hydroxy; $C_1$–$C_6$ alkoxy; or a methylene- or ethylene-dioxy group linked to positions 10 and 11 of the molecule; and the pharmaceutically acceptable salts thereof Examples of specific compounds according to the present invention are the following:

9-ethynyl-camptothecin (1);
9-phenylethynyl-camptothecin (2);
9-(dimethylaminopropyn-1-yl)-camptothecin (3);
9-hydroxypropyn-1-yl-camptothecin (4);
9-trimethylsilylethynyl-camptothecin (5);
9-cyclopentylethynyl-camptothecin (6);
9-cyclohexylpropyn-1-yl-camptothecin (7);
9-hexyn-1-yl-camptothecin (8);
7-ethyl-9-ethynyl-camptothecin (9);
7-ethyl-9-phenylethynyl-camptothecin (10);
7-ethyl-9-(dimethylaminopropyn-1-yl)-camptothecin (11);
7-ethyl-9-hydroxypropyn-1-yl-camptothecin (12);
7-ethyl-9-trimethylsilylethynyl-camptothecin (13);
7-ethyl-9-cyclopentylethynyl-camptothecin (14);
7-ethyl-9-cyclohexylpropyn-1-yl-camptothecin (15);
7-ethyl-9-hexyn-1-yl-camptothecin (16);
9-(4-methoxyphenyl-ethynyl)-camptothecin (17);
9-(3-tosylamino-phenylethynyl)-camptothecin (18);
9-[3-(2,5-dimethyl-pyrrol-1-yl)phenylethynyl]-camptothecin (19);
9-(4-chlorophenyl-ethynyl)-camptothecin (20);
9-(N-benzyl-N-methylamino-propyn-1-yl)-camptothecin (21);
9-(5-phenyl-pentyn-1-yl)-camptothecin (22);
9-(3-phenoxy-propyn-1-yl)-camptothecin (23);
9-[(6-methoxy-naphth-2-yl)-ethynyl]-camptothecin (24);
9-(3-hydroxy-3-methyl-butyn-1-yl)-camptothecin (25);
9-(3-methoxy-propyn-1-yl)-camptothecin (26);
9-(diethylamino-propyn-1-yl)-camptothecin (27);
9-(methylamino-propyn-1-yl)-camptothecin (28);
9-(3,3-dimethyl-butyn-1-yl)-camptothecin (29);
9-(3-aminophenyl-ethynyl)-camptothecin (30);
10-ethynyl-camptothecin (31);
10-phenylethynyl-camptothecin (32);
10-(dimethylamino-propyn-1-yl)-camptothecin (33);
10-hydroxypropyn-1-yl-camptothecin (34);
10-trimethylsilylethynyl-camptothecin (35);
10-cyclopentylethynyl-camptothecin (36);
10-cyclohexylpropyn-1-yl-camptothecin (37);
10-hexyn-1-yl-camptothecin (38);
7-ethyl-10-ethynyl-camptothecin (39);
7-ethyl-10-phenylethynyl-camptothecin (40);
7-ethyl-10-dimethylamino-propyn-1-yl-camptothecin (41);
7-ethyl-10-hydroxypropyn-1-yl-camptothecin (42);
7-ethyl-10-trimethylsilylethynyl-camptothecin (43);
7-ethyl-10-cyclopentylethynyl-camptothecin (44);
7-ethyl-10-cyclohexylpropyn-1-yl-camptothecin (45);
7-ethyl-10-hexyn-1-yl-camptothecin (46);

and, where a salifiable substituent is present on the molecule framework, their pharmaceutically acceptable salts. With reference to the above formula (I), the structural formulae of the above listed compounds are reported in the following Tables 1 and 2.

TABLE 1

9-substituted compounds of formula (I)

| Compound | $R_1$ | $R_2$ | X |
|---|---|---|---|
| 1 | H | H | H |
| 2 | Ph | H | H |
| 3 | —$CH_2N(CH_3)_2$ | H | H |
| 4 | —$CH_2OH$ | H | H |
| 5 | —$Si(CH_3)_3$ | H | H |
| 6 | 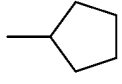 | H | H |
| 7 | | H | H |

TABLE 1-continued 9-substituted compounds of formula (I)

| Compound | R₁ | R₂ | X |
|---|---|---|---|
| 8 | n-C₄H₉ | H | H |
| 9 | H | Et | H |
| 10 | Ph | Et | H |
| 11 | —CH₂N(CH₃)₂ | Et | H |
| 12 | —CH₂OH | Et | H |
| 13 | —Si(CH₃)₃ | Et | H |
| 14 | (cyclopentyl) | Et | H |
| 15 | (ethylcyclohexyl) | Et | H |
| 16 | n-C₄H₉ | Et | H |
| 17 | p.CH₃O—Ph— | H | H |
| 18 | m.(TsNH)—Ph— | H | H |
| 19 | (2,5-dimethyl-N-(m-tolyl)pyrrole) | H | H |
| 20 | p.Cl—Ph— | H | H |
| 21 | —CH₂N(CH₃)Bz | H | H |
| 22 | —(CH₂)₃—Ph | H | H |
| 23 | —CH₂—OPh | H | H |
| 24 | (6-methyl-2-methoxynaphthalene) | H | H |
| 25 | —C(OH)(CH₃)₂ | H | H |
| 26 | —CH₂—OCH₃ | H | H |
| 27 | —CH₂N(Et)₂ | H | H |
| 28 | —CH₂—NHCH₃ | H | H |
| 29 | —C(CH₃)₃ | H | H |
| 30 | m.H₂N—Ph— | H | H |

TABLE 2

10-substituted compounds of formula (I)

| Compound | R₁ | R₂ | X |
|---|---|---|---|
| 31 | H | H | H |
| 32 | Ph | H | H |
| 33 | —CH₂N(CH₃)₂ | H | H |
| 34 | —CH₂OH | H | H |
| 35 | —Si(CH₃)₃ | H | H |
| 36 | (cyclopentyl) | H | H |
| 37 | (ethylcyclohexyl) | H | H |
| 38 | n-C₄H₉ | H | H |
| 39 | H | Et | H |
| 40 | Ph | Et | H |
| 41 | —CH₂N(CH₃)₂ | Et | H |
| 42 | —CH₂OH | Et | H |
| 43 | —Si(CH₃)₃ | Et | H |
| 44 | (cyclopentyl) | Et | H |
| 45 | (ethylcyclohexyl) | Et | H |
| 46 | n-C₄H₉ | Et | H |

In Tables 1 and 2, the symbols Et, Ph, Bz and Ts stand for ethyl, phenyl, benzyl and tosyl, respectively; the symbols m and p stand for meta and para substituent onto phenyl ring, respectively.

The present invention relates also to a process for preparing the compounds of formula (I) as defined above, said process comprising:

(a) reacting a compound of formula (II)

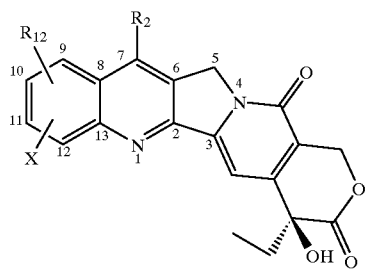

wherein:
$R_{12}$ is selected from: a halogen atom; a group —$OSO_2R_{13}$ wherein $R_{13}$ is $C_1$–$C_5$ alkyl, optionally substituted at the terminal carbon atom by one, two or three halogen atoms; and an optionally substituted phenyl ring;

$R_2$ is selected from: hydrogen; $C_1$–$C_6$ alkyl; $C_3$–$C_7$ cycloalkyl; and phenyl $C_1$–$C_6$ alkyl; and X is selected from: hydrogen; $C_1$–$C_6$ alkyl; $C_3$–$C_7$ cycloalkyl; $C_1$–$C_6$ alkoxy; $C_3$–$C_7$ cycloalkoxy; $C_1$–$C_6$ alkanoyloxy; benzoyloxy; amino; hydroxy; nitro; chlorine; and a methylene- or ethylene-dioxy group linked to positions 10 and 11 of the molecule; with a compound of formula (III):

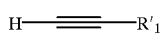

wherein $R'_1$ is selected from: an optionally substituted $C_1$–$C_6$ alkyl; $C_3$–$C_7$ cycloalkyl; $C_3$–$C_7$ cycloalkyl $C_1$–$C_6$ alkyl; phenyl $C_1$–$C_6$ alkyl; an optionally substituted phenyl; an optionally substituted naphthyl; —$R_x$—$NR_3R_4$, wherein $R_x$ is $C_1$–$C_4$ alkylene, $R_3$ and $R_4$ are, each independently, hydrogen, $C_1$–$C_6$ alkyl, phenyl, or benzyl; —$(R_y)_m$—$COOR_5$, wherein m is zero or 1, $R_y$ is $C_1$–$C_4$ alkylene, $R_5$ is hydrogen, $C_1$–$C_6$ alkyl, $C_3$–$C_7$ cycloalkyl, or phenyl $C_1$–$C_6$ alkyl; —$(R_z)_n$—$COR_6$, wherein n is zero or 1, $R_z$ is $C_1$–$C_4$ alkylene, $R_6$ is $C_1$–$C_6$ alkyl, $C_3$–$C_7$ cycloalkyl, phenyl $C_1$–$C_6$ alkyl, an optionally substituted phenyl, or —$NR_7R_8$, wherein $R_7$ and $R_8$ are, each independently, hydrogen or $C_1$–$C_6$ alkyl; and —$SiR_9R_{10}R_{11}$, wherein $R_9$, $R_{10}$ and $R_{11}$ are, each independently, $C_1$–$C_4$ alkyl; so obtaining the corresponding compound of formula (I); and (b) when $R'_1$ is —$SiR_9R_{10}R_{11}$, optionally removing the —$SiR_9R_{10}R_{11}$ group by acid treatment so obtaining the corresponding compound of formula (I) having $R_1$ equal to hydrogen; and (c) if necessary, converting the so obtained compound of formula (I) into a pharmaceutically acceptable salt thereof.

The starting compounds of formula (II) have a 20(S)-configuration which is retained through the process leading to the compounds of formula (I). The compounds of formula (II) are typically free of the corresponding 20(R)-isomers. However, said process may be applied to a racemic mixture of a compound of formula (II) and the corresponding 20(R)-isomer. In that case, a racemic mixture of a compound of formula (I) and a 20(R)-isomer of a compound of formula (I) is obtained.

When one or more new stereogenic centers are present in $R_1$, all the possible isomers, diastereoisomers, epimers, and geometric isomers, are included in the present disclosure.

The reaction of step (a) may be performed in a suitable solvent, in the presence of catalytic amounts, i.e. from 0.0001 to 0.2 molar equivalents, of a compound of formula

wherein:
M is a transition metal, preferably palladium, nickel or platinum;

L and L', which may be the same or different from each other, are anions, such as, e.g. halide or acetate, or neutral molecules, such as, e.g., solvent molecules, phosphines, phosphites or diamines; and q and r are numbers from 0 to 4; provided that q+r is at least 1.

The reaction of step (a) may be optionally carried out in the presence of a Cu(I) compound as co-catalyst, such as, e.g., a Cu(I) halide, $Cu_2O$, CuCN, or a CuCN-LiCl complex, preferably CuI, CuCl, or $Cu_2O$.

The reaction temperature is generally from about −20° C. to about 200° C., preferably from about 20° C. to about 100° C., while the reaction time may vary from a few minutes to several days, such as, e.g., from 5 minutes to 3 days, preferably from about one hour to about one day. The reaction may be optionally carried out in the presence of a suitable organic or inorganic base, and of a lithium halide, such as, e.g., LiCl or LiBr.

Suitable solvents for step (a) may be, e.g., dimethylformamide (DMF), acetonitrile, dimethylsulphoxide (DMSO), $CHCl_3$, dioxane, tetrahydrofuran (THF), or mixtures thereof. Suitable inorganic bases include, e.g., alkali or alkaline-earth metal salts, such as, for example, $NaHCO_3$, $Na_2CO_3$, or NaOAc. Suitable organic bases may be, for example, trialkyalmines, such as, e.g., triethylamine or diisopropylethylamine; or heteroaromatic bases such as, e.g., pyridine, or 2,6-di-$C_1$–$C_6$ alkyl-substituted pyridines, such as, e.g., 2,6-lutidine.

L and L' may be, e.g., halides; acetates; phosphines, such as, e.g., triphenylphosphine or chelating diphosphines, such as, e.g., bis(diphenylphosphino)methane, 1,2- and 1,3-bis (diphenyl phosphino)propane, 1,4-bis(diphenylsphsphino) butane or 1,1'-bis(diphenylphosphino)ferrocene (DPPF). The molar ratio between the transition metal and the ligands L and L' is generally from 1:1 to 1:4.

The reaction of optional step (b), wherein the —$SiR_9R_{10}R_{11}$ group is removed by acid treatment so obtaining the corresponding compound of formula (I) having $R_1$ equal to hydrogen, may be carried out with a suitable strong acid, e.g. trifluoroacetic acid.

The starting materials of formulas (II) and (III) are known compounds, or may be obtained following known methods. For instance, 9-halogen-, 10-halogen-, 11-halogeno-, and 12-halogeno-camptothecins may be prepared according, to Sawada, S. et al., Chem. Pharm. Bull. 3, 3183–3188 (1991).

For instance, 10-hydroxy-, 10-methoxy-, and 10,11-methylendioxy-9-halogen-camptothecins may be prepared starting from the corresponding 10- or 10,11-substituted-9-amino-derivatives, prepared by known procedures (see, for instance, Wall et al., J. Med. Chem. 36, 2689–2700, (1993), or Wani et al. J. Med. Chem. 29, 2358–2363, (1986)), and then following the above cited reference.

For instance, 9-trifluoromethansulfonyloxy camptothecin, 10-trifluoromethansulfonyloxy camptothecin, 10,11-trifluoromethansulfonyloxy camptothecin, 12-trifluoromethansulfonyloxy camptothecin, 10-hydroxy-9-trifluoromethansulfonyloxycamptothecin, 10-methoxy-9-trifluoromethansulfonyloxycamptothecin, 10,11-methylendioxy-9- trifluoromethansulfonyloxy camptothecin, 10-p-toluensulfonyloxy camptothecin, 11-p-toluensulfonyloxy camptothecin, 12-p-toluensulfonyloxy camptothecin, 10-hydroxy-9-p-toluensulfonyloxy camptothecin, 10-methoxy-9-p-toluensulfonyloxy camptothecin and 10,11-methylendioxy-9-p-toluensulfonyloxy camptothecin, may be prepared from the corresponding hydroxy derivatives obtained, in turn, as described in the references cited above, by treatment with suitable sulfonylating agents.

PHARMACOLOGY

The compounds of the present invention are endowed with antitumor activity, for example against leukaemia and solid tumors such as, for example, colon and rectal tumors. The antitumor activity of the compounds of the present invention is shown, for example, by the fact that they have been found to possess antileukaemic activity when tested according to the method described in J. Med. Chem. 36, 2689 (1993), using the L1210 murine lymphoid leukemia model.

A human or animal body in need thereof may thus be treated by a method which comprises the administration thereto of a pharmaceutically effective amount of a compound of formula (I) or a pharmaceutically acceptable salt thereof.

The present invention further provides pharmaceutical compositions comprising a camptothecin derivative of formula (I) as defined above, or a pharmaceutically acceptable salt thereof, as an active principle, in association with one or more pharmaceutically acceptable carriers and/or diluents.

These pharmaceutical compositions may contain any quantity of a camptothecin derivative of formula (I) which is effective to exhibit any antitumor activity in vivo. Typical in vivo doses are from 0.1 to 60 mg of camptothecin derivative per kg of body weight. A particularly preferred range is from 1 to 40 mg/kg. The camptothecin derivatives of the present invention may also be mixed with other active materials which do not impair the desired action and/or supplement the desired action.

The pharmaceutical compositions of the present invention may be administered by any route, for example, orally, parenterally, intravenously, intradermally, subcutaneously, or topically, in liquid or solid form. A preferred mode of administration is orally. Oral compositions will generally include an inert diluent or an edible carrier. They may be enclosed in gelatin capsules or compressed into tablets. For the purpose of oral therapeutic administration, the compounds of the present invention may be incorporated with excipients and used in the form of tablets, capsules, elixirs, syrups and the like. These preparations should contain at least 0,1% of active compound but may be varied depending upon the particular form.

The tablets, pills, capsules, troches and the like may contain the following ingredients: a binder such as microcrystalline cellulose, gumtragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; a sweetening agent such as sucrose or saccharin or flavouring agent such as peppermint, methyl salicylate, or orange flavouring may be added. When the dosage unit form is a capsule, it may contain, in addition to material of the above type, a liquid carrier such as fatty oil. Other dosage unit forms may contain other various materials which modify the physical form of the dosage unit, for example, as coatings. Thus tablets or pills may be coated with sugar shellac, or other enteric coating agents.

A syrup may contain, in addition to the active compounds, sucrose as a sweetening agent and certain preservatives, dyes and colouring and flavours.

Material used in preparing these various compositions should be pharmaceutically pure and non toxic in the amount used. For the purpose of parenteral therapeutic administration, the active ingredient may be incorporated into a solution or suspension.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulphite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic The dosage values will vary with the specific severity of the disease condition to be alleviated. Good results are achieved when the compounds described herein are administered to a subject requiring such treatment as an effective oral, parenteral or intravenous dose. It is to be understood that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

The following examples better illustratethe present invention, but cannot be construed as a limitation of the scope thereof. The number in brackets reported after the chemical name of the compounds prepared according to the following examples corresponds to the number given in Tables 1 and 2.

EXAMPLE 1

9-bromo-camptothecin.

2.15 g of $NaNO_2$ in 40 mL of $H_2O$ were dropped at 5° C. into a solution of 9 g of 9-amino-camptothecin in 850 mL of 16% HBr. After 1 hr at room temperature the solution was dropped in a flask containing 19 g of CuBr in 200 mL of 16% HBr at 70° C. The reaction mixture was kept at 70° C. for 2 hrs, then it was poured into cold water. The precipitate was filtered and the mother liquors were extracted with $CH_2Cl_2$; the organic extract, dried and evaporated, was combined with the precipitate and purified by flash chromatography (eluent:$CH_2Cl_2$/$CH_3OH$=95/5) to give 8.19 g of the title product (HPLC assay:97.3%).

$^2$H-NMR 400 MHz (DMSO-d6): δ (ppm) 8.87 (s, 1H), 8.20 (d, J=8.5 Hz, 1H), 8.06 (d, J=7.32 Hz, 1H), 7.81–7.75 (m, 1H), 7.35 (s, 1H), 6.53 (s, 1H), 5.42 (s, 2H), 5.32 (s, 2H), 1.89–1.82 (m, 2H), 0.87 (t, J=7.32 Hz, 3H).

MS (FD):$M^+$=427.

By analogous procedure starting from the corresponding amino derivatives, the following bromo derivatives were prepared:

10-bromo-camptothecin;

11-bromo-camptothecin;

12-bromo-camptothecin;

10-hydroxy-9-bromo-camptothecin;

10-methoxy-9-bromo-camptothecin; and 10,11-methylendioxy-9-bromo-camptothecin.

9-phenylethynyl-camptothecin (2).

0.1 g of 9-bromo-camptothecin prepared as described above were dissolved in 2 ml of DMF. In an argon atmosphere, 0.036 ml of triethylamine, 0.132 ml of phenylpropyne, 14.2 mg of 1,1'-bis (diphenylphosphino) ferrocene (DPPF), 5.2 mg of Pd(OAc)$_2$ and 2.2 mg of CuI were added sequentially. The reaction mixture was heated to 80° C. for 20 hrs monitoring by HPLC. CH$_2$Cl$_2$ and water were added and the organic phase was dried on Na$_2$SO$_4$ and evaporated. The crude product was purified by flash chromatography (eluent: CH$_2$Cl$_2$/MeOH=99.9/0.1) to give 96 mg of the title compound (HPLC assay: 95.6.)

$^1$H NMR 200 MHz (DMSO) δ (ppm) 0.87 (t, J=7.2 Hz, 3H), 1.85 (m, 2H), 5.35 (s, 2H), 5.43 (s, 2H), 6.54 (s, 1H), 7.36 (s, 1H), 7.48–7.78 (m, 5H), 7.92 (m, 1H), 7.97 (m, 1H), 8.23 (m, 1H), 9.10 (s, 1H)

MS (FD): (EHC=33 mA) m/z 449 (82, (MH)$^+$); 448 (100, (M)$^+$.

By analogous procedure and using the opportune starting materials, the following compounds were obtained:

9-ethynyl-camptothecin (1);

9-hydroxypropyn-1-yl-camptothecin (4);

9-cyclopentylethynyl-camptothecin (6);

9-cyclohexylpropyn-1-yl-camptothecin (7);

9-hexyn-1-yl-camptothecin (8);

7-ethyl-9-ethynyl-camptothecin (9);

7-ethyl-9-phenylethynyl-camptothecin (10);

7-ethyl-9-hydroxypropyn-1-yl-camptothecin (12);

7-ethyl-9-cyclopentylethynyl-camptothecin (14);

7-ethyl-9-cyclohexylpropyn-1-yl-camptothecin (15);

7-ethyl-9-hexyn-1-yl-camptothecin (16);

9-(4-methoxyphenyl-ethynyl)-camptothecin (17) $^1$H NMR 400 MHz (DMSO) δ (ppm) 0.84 (t, J=7.0 Hz, 3H), 1.80 (m, 1H), 3.79 (s, 3H), 5.31 (s, 2H), 5.39 (s, 2H), 6.50 (s, 1H), 7.02 (d, J=8.5 Hz, 2H), 7.33 (s, 1H), 7.68 (d, J=8.5 Hz, 2H), 7.84 (dd, J=8.0, 8.5 Hz, 1H), 7.90 (dd, J=8.0, 1.5 Hz, 1H), 8.16 (d, J=8.5 Hz, 1H), 9.50 (s, 1H);

9-(3-tosylamino-phenylethynyl)-camptothecin (18) $^1$H NMR 200 MHz (DMSO) δ (ppm) 0.87 (t, J=7.5 Hz, 3H), 1.84 (m, 2H), 2.33 (s, 3H), 5.34 (s, 2H), 5.42 (s, 2H), 6.53 (s, 1H), 7.0–7.5 (m, 7H), 7.68 (d, J=8.3 Hz, 2H), 7.87 (dd, J=7.3, 8.3 Hz, 1H), 7.98 (dd, J=1.3, 7.3 Hz, 1H), 8.23 (d, J=8.3 Hz, 1H), 9.00 (s, 1H), 10.47 (s, 1H) 9-[3-(2,5-dimethyl-pyrrol-1-yl)phenylethynyl]-camptothecin (19) $^1$H NMR 200 MHz (DMSO) δ (ppm) 0.87 (t, J=7.5 Hz, 3H), 1.86 (m, 2H), 2.01 (s, 6H), 5.33 (s, 2H), 5.42 (s, 2H), 5.83 (s, 2H), 6.54 (s, 1H), 7.36 (s, 1H), 7.38 (m, 1H), 7.64 (dd, J=8.0 Hz, 1H), 7.73 (dd, J=1.5 Hz, 1H), 7.82 (m, 1H), 7.90 (m, 1H), 8.02 (dd, J=1.5, 7.5 Hz, 1H), 8.24 (ddd, J=1.0, 1.5, 8.0 Hz, 1H), 9.32 (d, J=1.0 Hz, 1H);

9-(4-chlorophenyl-ethynyl)-camptothecin (20) $^1$H NMR 200 MHz (DMSO) 5 (ppm) 0.87 (t, J=7.3 Hz, 3H), 1.89 (m, 2H), 5.35 (s, 2H), 5.42 (s, 2H), 6.51 (s, 1H), 7.37 (s, 1H), 7.58 (d, J=8.6 Hz, 2H), 7.80 (d, J=8.6 Hz, 2H), 7.90 (m, 2H), 8.24 (m, 1H), 9.10 (s, 1H);

9-(N-benzyl-N-methylamino-propyn-1-yl)-camptothecin (21) $^1$H NMR 400 MHz (DMSO) δ (ppm) 0.88 (t, J=7.3 Hz, 3H), 1.86 (m, 2H), 2.38 (s, 3H), 3.68 (s, 2H), 3.70 (s, 2H), 5.34 (s, 2H), 5.41 (s, 2H), 6.50 (s, 1H), 7.2–7.4 (m, 6H), 7.83 (dd, J=7.3 Hz, 1H), 7.89 (dd, J=1.5, 7.3Hz, 1H), 8.18 (d, J=7.3 Hz, 1H), 8.90 (s, 1H);

9-(5-phenyl-pentyn-1-yl)-camptothecin (22) $^1$H NMR 200 MHz (DMSO) δ (ppm) 0.86 (t, J=7.3 Hz, 3H), 1.80 (m, 2H), 1.98 (m, 2H), 2.60 (m, 2H), 2.80 (m, 2H), 5.33 (s, 2H), 5.42 (s, 2H), 6.52 (s, 1H), 7.0–7.4 (m, 6H), 7.80 (m, 2H), 8.17 (m, 1H), 8.91 (s, 1H);

9-(3-phenoxy-propyn-1-yl)-camptothecin (23) $^1$H NMR 400 MHz (DMSO) δ (ppm) 0.82 (t, J=7.3 Hz, 3H), 1.80 (m, 2H), 5.20 (s, 2H), 5.24 (s, 2H), 5.38 (s, 2H), 6.49 (s, 1H), 6.98 (m, 1H), 7.12 (m, 2H), 7.34 (m, 2H), 7.30 (s, 1H), 7.79 (dd, J=7.0, 8.0 Hz, 1H), 7.82 (dd, J=2.0, 7.0 Hz, 1H), 8.16 (d, 8.0 Hz, 1H), 8.69 (s, 1H);

9-[(6-methoxy-naphth-2-yl)-ethynyl]-camptothecin (24) $^1$H NMR 200 MHz (DMSO) δ (ppm) 0.87 (t, J=7.5 Hz, 3H), 1.88 (m, 2H), 3.90 (s, 3H), 5.37 (s, 2H), 5.43 (s, 2H), 6.54 (s, 1H), 7.25 (dd, J=2.6, 8.9Hz, 1H) 7.37 (s, 1H), 7.40 (d, J=2.6 Hz, 1H), 7.7–8.0 (m, 5H), 8.22 (d, J=8.1 Hz, 1H), 8.30 (d, J=.0 Hz, 1H), 9.15 (s, 1H);

9-(3-hydroxy-3-methyl-butyn-1-yl)-camptothecin (25) $^1$H NMR 200 MHz (DMSO) δ (ppm) 0.87 (t, J=7.1 Hz, 3H), 1.59 (s, 6H), 1.86 (m, 2H), 5.35 (s, 2H), 5.42 (s, 2H), 5.68 (s, 1H), 6.53 (s, 1H), 7.35 (s, 1H) 7.80 (m, 2H), 8.17 (m, 1H), 8.90 (s, 1H);

9-(3-methoxy-propyn-1-yl)-camptothecin (26) $^1$H NMR 200 MHz (DMSO) δ (ppm) 0.87 (t, J=7.2 Hz, 3H), 1.87 (m, 2H), 3.42 (s, 3H), 5.32 (s, 2H), 5.42 (s, 2H), 6.50 (s, 1H), 7.34 (s, 1H), 7.90 (m, 2H), 8.20 (m, 1H), 8.88 (s, 1H);

9-(diethylamino-propyn-1-yl)-camptothecin (27) $^1$H NMR 200 MHz (DMSO) δ (ppm) 0.87 (t, J=7.2 Hz, 3H), 1.34 (t, J=7.2 Hz, 6H), 1.87 (m, 2H), 3.30 (m, 4H), 4.51 (s, 2H), 5.30 (s, 2H), 5.42 (s, 2H), 6.52 (bs, 1H), 7.34 (s, 1H), 7.86 (dd, J=7.5, 8.1 Hz, 1H), 7.96 (dd, J=1.3, 7.5 Hz, 1H), 8.25 (d, J=8.1 Hz, 1H), 9.12 (s, 1H), 11.23 (bs, 1H);

9-(methylamino-propyn-1-yl)-camptothecin (28) $^1$H NMR 200 MHz (DMSO) δ (ppm) 0.87 (t, J=7.2 Hz, 3H), 1.87 (m, 2H), 2.44 (s, 3H), 3.69 (s, 2H), 5.32 (s, 2H), 5.42 (s, 2H), 6.51 (s, 1H), 7.34 (s, 1H), 7.80 (m, 2H), 8.16 (m, 1H), 8.92 (s, 1H);

9-(3,3-dimethyl-butyn-1-yl)-camptothecin (29) $^1$H NMR 400 MHz (DMSO) δ (ppm) 0.87 (t, J=7.3 Hz, 3H), 1.42 (s, 9H), 1.86 (m, 2H), 5.34 (s, 2H), 5.42 (s, 2H), 6.53 (s, 1H), 7.34 (s, 1H), 7.80 (m, 2H) 8.10 (m, 1H), 8.85 (s, 1H);

9- (3-aminophenyl-ethynyl)-camptothecin (30) $^1$H NMR 400 MHz (DMSO) δ (ppm) 0.87 (t, J=7.2 Hz, 3H), 1.86 (m, 2H), 5.30 (s, 2H), 5.35 (s, 2H), 5.42 (s, 2H), 6.53 (s, 1H), 6.66 (dd, J=2.1, 8.1 Hz, 1H), 6.90 (m, 2H), 7.10 (dd, J=8.1 Hz, 1H), 7.36 (s, 1H), 7.87 (dd, J=8.5 Hz, 1H), 7.94 (dd, J=1.3, 8.5 Hz, 1H), 8 20 (d, J=8.5 Hz, 1H), 9.02 (s, 1H);

10-ethynyl-camptothecin (31);

10-phenylethynyl-camptothecin (32);

10-hydroxypropyn-1-yl-camptothecin (34);

10-cyclopentylethynyl-camptothecin (36);

10-cyclohexylpropyn-1-yl-camptothecin (37);

10-hexyn-1-yl-camptothecin (38);

7-ethyl-10-ethynyl-camptothecin (39);

7-ethyl-10-phenylethynyl-camptothecin (40);

7-ethyl-10-hydroxypropyn-1-yl-camptothecin (42);

7-ethyl-10-cyclopentylethynyl-camptothecin (44);

7-ethyl-lo-cyclohexylpropyn-1-yl-camptothecin (45); and 7-ethyl-10-hexyn-1-yl-camptothecin (46).

EXAMPLE 2

9-trimethylsilylethynyl-camptothecin (5).

0.144 g of 9-bromo-camptothecin prepared as described in Example 1 were dissolved in 2 ml of DMF. In an argon atmosphere, 0.036 ml of triethylamine, 0.19 ml of trimethylsilyl-acetylene, 16.1 mg of DPPF, 6 mg of Pd(OAc)$_2$ and 2.6 mg of CuI were added sequentially. The reaction mixture was heated to 50° C. for 16 hrs monitoring by HPLC. CH$_2$Cl$_2$ and water were added and the organic phase was dried on Na$_2$SO$_4$ and evaporated. The crude product was purified by flash chromatography (eluent: CH$_2$Cl$_2$/MeOH=99/1) to give 94 mg of a red lacquer (HPLC assay: 75%) which was suspended in Et$_2$O to give a beige powder. After decanting and washing with Et$_2$O twice, 90 mg of the title compound were obtained (HPLC assay: 82%).

¹H NMR 200 MHz (CDCl₃) δ (ppm) 0.32 (s, 9H), 1.00 (t, J=7.6 Hz, 3H), 1.85 (m, 2H), 3.70 (s, 1H) , 5.29–5.70 (m, 2H), 5.31 (s, 2H), 7.63 (s, 1H), 7.70 (m, 1H), 7.79 (m, 1H), 8.15 (m, 1H), 8.79 (s, 1H). MS (FAB+) : m/z 477 (8, (MNa)⁺) ; 445 (38, (MH)⁺; 400 (10, (M-CO₂)⁺) ; 373 (15, (M-SiMe₃+2H)⁺) : 73 (100, (SiMe₃)⁺).

By analogous procedure and using the opportune starting materials, the following compounds were obtained:

7-ethyl-9-trimethylsilylethynyl-camptothecin (13);

10-trimethylsilylethynyl-camptothecin (35); and 7-ethyl-10-trimethylsilylethynyl-camptothecin (43).

EXAMPLE 3

9-(dimethylaminopropyn-1-yl)-camptothecin (3).

0.12 g of 9-bromo-camptothecin prepared as described in Example 1 were dissolved in 2 ml of DMF. In an argon atmosphere, 0.044 ml of triethylamine, 0.15 ml of 3-N,N-dimethylaminopropyne, 17 mg of DPPF, 6.2 mg of Pd(OAc)₂ and 2.6 mg of CuI were added sequentially. The reaction mixture was heated to 70° C. for 18 hrs monitoring by HPLC. CH₂Cl₂ and brine were added, then the organic phase was treated with an equal volume of HCl 10%; the aqueous layer was washed once with CH₂Cl₂, then treated with NaOH till pH=5 and extracted three times with an equal volume of CH₂Cl₂. The collected organic phases were dried on Na₂SO₄ and evaporated to give 35 mg of the title compound (HPLC assay: 91%). ¹H NMR 400 MHz (DMSO) δ (ppm) 0.87 (t, J=7 6 Hz, 3H) , 1.86 (m, 2H), 2.33 (s, 6H), 3.65 (s, 2H), 5.34 (s, 2H), 5.42 (s, 2H), 6.50 (s, 1H), 7.35 (s, 1H), 7.83 (m, 1H), 7.87 (m, 1H), 8.19 (m, 1H), 8.90 (s, 1H)

MS (FAB+): m/z 430 (100, (MH)⁺; 386 (18, (MH-CO₂)+) ; 385 (19, (M-CO₂)⁺); 58 (79, (CH₂NMe₂)⁺).

By analogous procedure and using the opportune starting materials, the following compounds were obtained:

7-ethyl-9-(dimethylaminopropyn-1-yl)-camptothecin (11);

10-(dimethylaminopropyn-1-yl)-camptothecin (33); and 7-ethyl-10-(dimethylaminopropyn-1-yl)-camptothecin (41).

What is claimed is:

1. A pharmaceutical composition, which comprises an effective amount of an alkynyl-substituted camptothecin of formula (I)

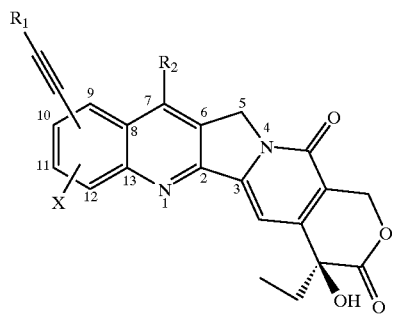

(I)

wherein R¹ is selected from the group consisting of:

hydrogen;

an optionally substituted $C_1$–$C_6$ alkyl;

$C_3$–$C_7$ cycloalkyl;

$C_3$–$C_7$ cycloalkyl $C_1$–$C_6$ alkyl;

an optionally substituted phenyl;

an optionally substituted naphthyl;

—$R_x$—$NR_3R_4$, wherein $R_x$ is $C_1$–$C_4$ alkylene, $R_3$ and $R_4$ are, each independently, hydrogen, $C_1$–$C_6$ alkyl phenyl, or benzyl;

—$(R_y)_m$—$COOR_5$, wherein m is zero or 1, $R_y$ is $C_1$–$C_4$ alkylene, $R_5$ is hydrogen, $C_1$–$C_6$ alkyl, $C_3$–$C_7$ cycloalkyl or phenyl $C_1$–$C_6$ alkyl;

—$(R_z)_n$—$COR_6$, wherein n is zero or 1, $R_z$ is $C_1$–$C_4$ alkylene, $R_6$ is $C_1$–$C_6$ alkyl, $C_3$–$C_7$ cycloalkyl, phenyl $C_1$–$C_6$ alkyl, an optionally substituted phenyl, or —$NR_7R_8$, wherein $R_7R_8$ are, each independently, hydrogen or $C_1$–$C_6$ alkyl; and $SiR_9$ $R_{10}R_{11}$, wherein $R_{10}$ and $R_{11}$ are, each independently, $C_1$–$C_4$ alkyl;

$R_2$ is selected from the group consisting of:

hydrogen; $C_1$–$C_6$ alkyl; $C_3$–$C_7$ cycloalkyl; and phenyl $C_1$–$C_6$ alkyl;

X is selected from the group consisting of:

alkanoyloxy; benzoyloxy; amino; hydroxy; nitro; chlorine; and a methylene- or ethylene-dioxy group linked to positions 10 and 11 of the molecule;

or a pharmaceutically acceptable salt thereof as an active principle for treatment of tumors, in association with one or more pharmaceutically acceptable carriers and/or diluents.

2. A method of treating tumors in a human or animal sensitive to camptothecin comprising administering an effective amount of the pharmaceutical composition of claim 1 to a human or animal in need thereof.

3. A process for preparing the pharmaceutical composition of claim 1, comprising mixing the alkynyl-substituted camptothecin of formula (I):

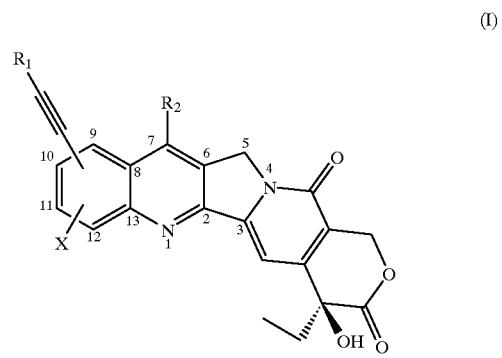

(I)

and one or more pharmaceutically acceptable carriers and/or diluents, wherein the alkynyl-substituted camptothecin is prepared by the process comprising:

(a) reacting a compound of formula (II)

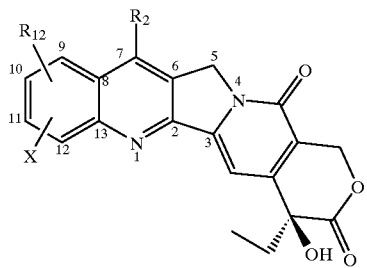

(II)

wherein:
R$_{12}$ is selected from the group consisting of a halogen atom; a group —OSO$_2$R$_{13}$ wherein R$_{13}$ is C$_1$–C$_5$ alkyl, optionally substituted at the terminal carbon atom by one, two or three halogen atoms; and an optionally substituted phenyl ring;

R$_2$ is selected from the group consisting of hydrogen; C$_1$–C$_6$ alkyl; C$_3$–C$_7$ cycloalkyl; and phenyl C$_1$–C$_6$ alkyl; and X is selected from the group consisting of hydrogen; C$_1$–C$_6$ alkyl; C$_3$–C$_7$ cycloalkyl; C$_1$–C$_6$ alkoxy; C$_3$–C$_7$ cycloalkoxy; C$_1$–C$_6$ alkanoyloxy; benzoyloxy; amino; hydroxy; nitro; chlorine; and a methylene- or ethylene-dioxy group linked to positions 10 and 11 of the molecule;

with a compound of formula (III):

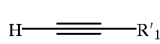

(III)

wherein R'$_1$ is selected from: an optionally substituted C$_1$–C$_6$ alkyl; C$_3$–C$_7$ cycloalkyl; C$_3$–C$_7$ cycloalkyl C$_1$–C$_6$ alkyl; phenyl C$_1$–C$_6$ alkyl; an optionally substituted phenyl; an optionally substituted napthyl; —R$_x$—NR$_3$R$_4$, wherein R$_x$ is C$_1$–C$_4$ alkylene, R$_3$ and R$_4$ are, each independently, hydrogen, C$_1$–C$_6$ alkyl, phenyl, or benzyl; —(R$_y$)$_m$—COOR$_5$, wherein m is zero or 1, R$_y$ is C$_1$–C$_4$ alkylene, R$_5$ is hydrogen, C$_1$–C$_6$ alkyl, C$_3$–C$_7$ cycloalkyl, or phenyl C$_1$–C$_6$ alkyl, an optionally substituted phenyl, or —NR$_7$R$_8$, wherein R$_7$ and R$_8$, are, each independently, hydrogen or C$_1$–C$_6$ cycloalkyl; and —SiR$_9$R$_{10}$R$_{11}$, wherein R$_9$, R$_{10}$, and R$_{11}$ are, independently, C$_1$–C$_4$ alkyl; so obtaining the corresponding compound of formula (I); and (b) when R'$_1$ is —SiR$_9$R$_{10}$R$_{11}$, optionally removing the —SiR$_9$R$_{10}$R$_{11}$ group by acid treatment so obtaining the corresponding compound of formula (I) having R$_1$ equal to hydrogen; and (c) optionally, converting the so obtained compound of formula (I) into a pharmaceutically acceptable salt thereof.

4. The process of claim 3, wherein the alkynyl-substituted camptothecin of formula (I):
R$_1$ is selected from the group consisting of:
hydrogen; C$_1$–C$_4$ alkyl; phenyl C$_1$–C$_6$ alkyl; phenyl; —R$_x$—NR$_3$R$_4$, wherein R$_x$ is a C$_1$–C$_4$ alkylene, R$_3$ and R$_4$ are, each independently, C$_1$–C$_4$ alkylene, R$_3$ and R$_4$ are, each independently, C$_1$–C$_4$ alkyl; —(R$_y$)$_m$ —COOR$_5$, wherein m is zero or 1, R$_y$ is a C$_1$–C$_4$ alkylene, R$_5$ is hydrogen or C$_1$–C$_4$ alkyl; and —(R$_z$)$_n$ —COR$_6$, wherein n is zero or 1, R$_z$ is a C$_1$–C$_4$ alkylene, R$_6$ is C$_1$–C$_6$ alkyl, phenyl, or —NR$_7$R$_8$, wherein R$_7$ and R$_8$ are hydrogen; and —SiR$_9$R$_{10}$R$_{11}$, wherein R$_9$, R$_{10}$ and R$_{11}$ are methyl or ethyl;

R$_2$ is hydrogen or C$_1$–C$_4$ alkyl;

X is selected from the group consisting of:
hydrogen; amino; hydroxy; C$_1$–C$_6$ alkoxy; or a methylene- or ethylene-dioxy group linked to positions 10 and 11 of the molecule;

or a pharmaceutically acceptable salt thereof.

5. The process of claim 3, wherein the alkynyl-substituted camptothecin of formula (1) is selected from the group consisting of:
9-ethynyl-camptothecin;
9-phenylethynyl-camptothecin;
9-(dimethylaminopropyn-1-yl)-camptothecin;
9-hydroxypropyn-1-yl-camptothecin;
9-trimethylsilylethynyl-camptothecin;
9-cyclopentylethynyl-camptothecin;
9-cyclohexylpropyn-1-yl-camptothecin;
9-hexyn-1-yl-camptothecin;
7-ethyl-9-ethynyl-camptothecin;
7-ethyl-9-phenylethynyl-camptothecin;
7-ethyl-9-(dimethylaminopropyn-1-yl)-camptothecin;
7-ethyl-9-hydroxypropyn-1-yl-camptothecin;
7-ethyl-9-trimethylsilylethynyl-camptothecin;
7-ethyl-9-cyclopentylethynyl-camptothecin;
7-ethyl-9-cyclohexylpropyn-1-yl-camptothecin;
7-ethyl-9-hexyn-1-yl-camptothecin;
9-(4-methoxyphenyl-ethynyl)-camptothecin;
9-(3-tosylamino-phenylethynyl)-camptothecin;
9-[3-(2,5-dimethyl-pyrrol-1-yl)phenylethynyl]-camptothecin;
9-(4-chlorophenyl-ethynyl)-camptothecin;
9-(N-benzyl-N-methylamino-propyn-1-yl)-camptothecin;
9-(5-phenyl-pentyn- 1 -yl)-camptothecin;
9-(3-phenoxy-propyn- 1 -yl)-camptothecin;
9-[(6-methoxy-naphth-2-yl)-ethynyl)-camptothecin;
9-(3-hydroxy-3-methyl-butyn- 1-yl)-camptothecin;
9-(3-methoxy-propyn- 1-yl)-camptothecin;
9-(diethylamino-propyn- 1-yl)-camptothecin;
9-(methylamino-propyn- 1-yl)-camptothecin;
9-(3,3-dimethyl-butyn- -yl)-camptothecin;
9-(3-aminophenyl-ethynyl)-camptothecin;
10-ethynyl-camptothecin;
10-phenylethynyl-camptothecin;
10-(dimethylamino-propyn-1-yl)-camptothecin;
10-hydroxypropyn-1-yl-camptothecin;
10-trimethylsilylethynyl-camptothecin;
10-cyclopentylethynyl-camptothecin;
10-cyclohexylpropyn-1-yl-camptothecin;
10-hexyn-1-yl-camptothecin;
7-ethyl-10-ethynyl-camptothecin;
7-ethyl-10-phenylethynyl-camptothecin;
7-ethyl-10-dimethylamino-propyn-1-yl-camptothecin;
7-ethyl-10-hydroxypropyn-1-yl-camptothecin;
7-ethyl-10-trimethylsilylethynyl camptothecin;
7-ethyl-10-cyclopentylethynyl-camptothecin;
7-ethyl-10-cyclohexylpropyn-1-yl-camptothecin;
7-ethyl-10-hexyn-1-yl-camptothecin;

or a pharmaceutically acceptable salt thereof.

6. The pharmaceutical composition of claim 1, wherein in the alkynyl-substituted camptothecin of formula (I):

$R_1$ is selected from the group consisting of:
hydrogen; $C_1$–$C_4$ alkyl; phenyl $C_1$–$C_6$ alkyl; phenyl; —$R_x$—$NR_3R_4$, wherein $R_x$ is a $C_1$–$C_4$ alkylene, $R_3$ and $R_4$ are, each independently, $C_1$–$C_4$ alkylene, $R_3$ and $R_4$ are, each independently, $C_1$–$C_4$ alkyl; —$(R_y)_m$—$COOR_5$, wherein m is zero or 1, $R_y$ is a $C_1$–$C_4$ alkylene, $R_5$ is hydrogen or $C_1$–$C_4$ alkyl; and —$(R_z)$—$COR_6$, wherein n is zero or 1, $R_z$ is a $C_1$–$C_4$ alkylene, $R_6$ is $C_1$–$C_6$ alkyl, phenyl, or —$NR_7R_8$, wherein $R_7$ and $R_8$ are hydrogen; and —$SiR_9R_{10}R_{11}$, wherein $R_9$, $R_{10}$ and $R_{11}$ are methyl or ethyl;

$R_2$ is hydrogen or $C_1$–$C_4$ alkyl;

X is selected from the group consisting of:
hydrogen; amino; hydroxy; $C_1$–$C_6$ alkoxy; or a methylene- or ethylene-dioxy group linked to positions 10 and 11 of the molecule;

or a pharmaceutically acceptable salt thereof.

7. The pharmaceutical composition of claim 1, wherein the alkynyl-substituted camptothecin of formula (I) is selected from the group consisting of:

9-ethynyl-camptothecin;
9-phenylethynyl-camptothecin;
9-(dimethylaminopropyn-1-yl)-camptothecin;
9-hydroxypropyn-1-yl-camptothecin;
9-trimethylsilylethynyl-camptothecin;
9-cyclopentylethynyl-camptothecin;
9-cyclohexylpropyn-1-yl-camptothecin;
9-hexyn-1-yl-camptothecin;
7-ethyl-9-ethynyl-camptothecin;
7-ethyl-9-phenylethynyl-camptothecin;
7-ethyl-9-(dimethylaminopropyn-1-yl)-camptothecin;
7-ethyl-9-hydroxypropyn-1-yl-camptothecin;
7-ethyl-9-trimethylsilylethynyl-camptothecin;
7-ethyl-9-cyclopentylethynyl-camptothecin;
7-ethyl-9-cyclohexylpropyn-1-yl-camptothecin;
7-ethyl-9-hexyn-1-yl-camptothecin;
9-(4-methoxyphenyl-ethynyl)-camptothecin;
9-(3-tosylamino-phenylethynyl)-camptothecin;
9-[3-(2,5dimethyl-pyrrol-1-yl)phenylethynyl]-camptothecin;
9-(4-chlorophenyl-ethynyl)-camptothecin;
9-(N-benzyl-N-methylamino-propyn-1-yl)-camptothecin;
9-(5-phenyl-pentyn-1-yl)-camptothecin;
9-(3-phenoxy-propyn-1-yl)-camptothecin;
9-[(6-methoxy-naphth-2-yl)ethynyl]-camptothecin;
9-(3-hydroxy-3-methyl-butyn-1-yl)-camptothecin;
9-(3-methoxy-propyn-1-yl)-camptothecin;
9-(diethylamino-propyn-1-yl)-camptothecin;
9-(methylamino-propyn-1-yl)-camptothecin;
9-(3,3-dimethyl-butyn-1-yl)-camptothecin;
9-(3-aminophenyl-ethynyl)-camptothecin;
10-ethynyl-camptothecin;
10-phenylethynyl-camptothecin;
10-(dimethylamino-propyn-1-yl)-camptothecin;
10-hydroxypropyn-1-yl-camptothecin;
10-trimethylsilylethynyl-camptothecin;
10-cyclopentylethynyl-camptothecin;
10-cyclohexylpropyn-1-yl-camptothecin;
10-hexyn-1-yl-camptothecin;
7-ethyl-10-ethynyl-camptothecin;
7-ethyl-10-phenylethynyl-camptothecin;
7-ethyl-10-dimethylamino-propyn-1-yl-camptothecin;
7-ethyl-10-hydroxypropyn-1-yl-camptothecin;
7-ethyl-10-trimethylsilylethynyl-camptothecin;
7-ethyl-10-cyclopentylethynyl-camptothecin;
7-ethyl-10-cyclohexylpropyn-1-yl-camptothecin;
7-ethyl-10-hexyn-1-yl-camptothecin;
or a pharmaceutically acceptable salt thereof.

8. The method of claim 2, wherein said effective amount is 0.1 to 60 mg/kg.

9. The method of claim 2, wherein said effective amount is 1 to 40 mg/kg.

* * * * *